United States Patent [19]

Papenfuhs

[11] 4,370,483
[45] Jan. 25, 1983

[54] PROCESS FOR THE MANUFACTURE OF 2-HYDROXYBENZOTHIAZOLES

[75] Inventor: Theodor Papenfuhs, Frankfurt am Main, Fed. Rep. of Germany

[73] Assignee: Hoechst Aktiengesellschaft, Fed. Rep. of Germany

[21] Appl. No.: 258,604

[22] Filed: Apr. 29, 1981

[30] Foreign Application Priority Data

May 5, 1980 [DE] Fed. Rep. of Germany ....... 3017153

[51] Int. Cl.$^3$ .................................... C07D 239/88
[52] U.S. Cl. .................................. 548/165; 424/270
[58] Field of Search ..................... 548/165; 424/270

[56] References Cited

U.S. PATENT DOCUMENTS

| | | |
|---|---|---|
| 2,179,987 | 11/1939 | Duzce et al. |
| 2,915,525 | 12/1959 | Applegath et al. |
| 3,586,690 | 6/1971 | Kuber et al. ............... 548/165 |
| 3,586,691 | 6/1971 | Scott ......................... 548/165 |
| 3,658,835 | 4/1972 | Gates et al. |
| 3,775,333 | 11/1973 | Loffelman et al. |
| 4,150,027 | 4/1978 | D'Amico et al. ........... 548/165 |
| 4,252,963 | 2/1981 | Papenfuhs . |
| 4,293,702 | 10/1981 | Umemura et al. |

FOREIGN PATENT DOCUMENTS

| | | |
|---|---|---|
| 39483 | 11/1981 | European Pat. Off. |
| 615131 | 6/1935 | Fed. Rep. of Germany . |
| 2131366 | 6/1971 | Fed. Rep. of Germany . |
| 2924712 | 6/1979 | Fed. Rep. of Germany . |
| 1317561 | 8/1969 | United Kingdom . |

OTHER PUBLICATIONS

J. Chem. Soc. 1930, 128–135.
J. Org. Chem. 27, 477 (1962).
J. Chem. Soc. 1962, 230.
J. Chem. Soc. 1939, 470.
J. Chem. Soc. 1927, 2738.
Egypt J. Chem. 16, 335 (1973)*.
J. Chem. Soc. 1942, 304.
Chem. Ber. 12, 1128 (1879).
Chem. Ber. 13, 10 (1880).
J. Org. Chem. 30, 3618 (1965).
J. Am. Chem. Soc. JACS 71, 3349 (1949).
J. Am. Chem. Soc. JACS 74, 1081 (1952).
J. Chem. Soc. 1949, 3311.

*Primary Examiner*—Nicholas S. Rizzo
*Attorney, Agent, or Firm*—Connolly and Hutz

[57] ABSTRACT

A process for the manufacture of a 2-hydroxybenzothiazole compound which comprises treating a 2-aminobenzothiazole compound with an alkali metal hydroxide or alkaline earth metal hydroxide in a solvent or diluent stable to alkalis, in the absence of water or with substantial exclusion of water and cyclizing the alkali metal or alkaline earth metal salt of the ortho-mercapto-N-phenylurea compound so obtained, optionally without intermediate isolation, by treatment with an acid to give the 2-hydroxybenzothiazole compound. The process furnishes the final products with high yield and purity; waste water problems are excluded by this process.

5 Claims, No Drawings

PROCESS FOR THE MANUFACTURE OF 2-HYDROXYBENZOTHIAZOLES

The invention relates to the field of intermediates and provides an improved process for the manufacture of 2-hydroxybenzothiazoles.

2-Hydroxybenzothiazoles (or 2(3H)-benzothiazolones) are important intermediates in the industrial practice, which are described for example in German Offenlegungsschrift No. 2,924,712, British Pat. No. 1,317,561 and U.S. Pat. No. 3,775,333. Synthesis of this group of compounds so far has not succeeded in a satisfactory manner. Either it involves serious ecological problems, for example when thiophenols or their derivatives are used as starting materials, or the starting compounds for the synthesis, for example 2-halo-, 2-alkoxy- or 2-alkylsulfonylbenzothiazoles, are obtainable with difficulty only in the industrial practice.

In detail the following methods of manufacture are known from the literature:

(a) Cyclization of o-aminothiophenols with phosgene, carbon oxysulfide, urea or cyanate (J. Chem. Soc. 1930, 128-135; U.S. Pat. No. 2,915,525; German Offenlegungsschrift No. 2,131,366; J. Chem. Soc. 1962, 230).

(b) Catalytic-reductive cyclization of o-nitrothiophenols with carbon monoxide (J. Chem. Soc. 1927, 2738).

(c) Reaction of o-nitrochlorobenzenes with thioglycolic acid and cyclization of the thioether formed by means of acetic anhydride (Egypt J. Chem. 16, 335 (1973)).

(d) Oxidation of 2-mercaptobenzothiazoles to benzothiazole-2-sulfonates and acid hydrolysis thereof (German Patent Specification No. 615,131; U.S. Pat. No. 2,179,987; J. Org. Chem. 27, 477 (1962)).

(e) Splitting of benzothiazolyl-alkyl-thioethers with alkali or alcoholic iodine solution (J. Chem. Soc. 1939, 470, and 1942, 304)).

(f) Reaction of 2-halobenzothiazoles with water, formamide or phenol, and optionally subsequent hydrolysis or hydrogenolysis (Chem. Ber. 12, 1128 (1879), and 13, 10 (1880); J. Org. Chem. 30, 3618 (1965); U.S. Pat. No. 3,658,835).

(g) Ether splitting of 2-alkoxybenzothiazoles (J. Am. Chem. Soc. 71, 3349 (1949), and 74, 1081 (1952)).

(h) Acid hydrolysis of 2-alkylsulfonyl-benzothiazoles (J. Chem. Soc. 1949, 3311).

The process variants (a) through (e) have mercapto compounds as starting materials or their precursors, or depend thereon. Serious ecological problems arise in connection with the synthesis, handling and waste disposal of these mercapto compounds; furthermore, apart from the unsubstituted basis substances, easily obtainable starting materials for these mercapto compounds are generally missing, so that the scope of variation of these known processes is strictly limited.

On the other hand, the process variants (f) through (h) are practically of scientific interest only, since their starting compounds cannot be synthetized in a technologically feasible manner to give acceptable yields. On the contrary the starting products described for these operation modes are prepared, in usual manner, at best from the 2-hydroxybenzothiazoles which can be synthetized in accordance with this invention.

There was thus a considerable interest in a generally applicable, industrially feasible and improved process for the manufacture of 2-hydroxybenzothiazoles.

The present invention provides now a process for the manufacture of a 2-hydroxybenzothiazole compound which comprises treating a 2-aminobenzothiazole compound with an alkali metal hydroxide or alkaline earth metal hydroxide in a solvent or diluent stable to alkalis, in the absence of water or with substantial exclusion of water (that is, advantageously in the presence of 2.5 weight % at most, preferably 0.5 weight % at most, of water in the reaction mixture and relative thereto), and cyclizing the alkali metal or alkaline earth metal salt of the ortho-mercapto-N-phenylurea compound so obtained, optionally without intermediate isolation, by treatment with an acid to give the 2-hydroxybenzothiazole compound.

The reaction proceeds according to the following scheme:

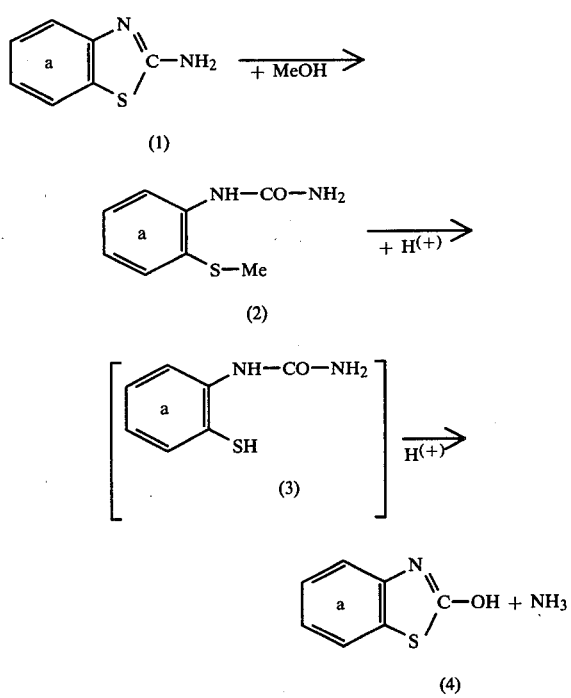

(in the formulae (1) through (4), Me is the equivalent of an alkali metal or alkaline earth metal, and the benzene nucleus a may carry further substituents; the ammonia set free in the cyclization is bound by the acid in the form of an ammonium ion).

The alkali metal or alkaline earth metal hydroxides MeOH are preferably barium, calcium or potassium hydroxide, especially sodium hydroxide. The acids used in the reaction for cyclization of the intermediates of the formula (2) are preferably mineral acids such as hydrochloric, sulfuric or phosphoric acid.

Solvents or diluents stable to alkalis which should be anhydrous and in which the ring cleavage of the 2-aminobenzothiazoles, optionally also the cyclization of the mercaptophenylureas formed therefrom, is carried out, are especially aliphatic monoalcohols or polyols, for example alkanols having from 1 to 6 carbon atoms, alkaneglycols having from 2 to 5 carbon atoms, alkanetriols having from 3 to 8 carbon atoms, high molecular weight alkanepolyols and lower monoalkyl ethers of the cited glycols, triols and polyols.

It was extremely surprising to state that the 2-aminobenzothiazoles easily obtainable on an industrial scale (see German Offenlegungsschrift No. 2,801,991) can be converted to 2-hydroxybenzothiazole compounds in a simple manner and with high yield and purity while using commercially available, cheap chemicals not raising any waste water problems. For, it is known from Chem. Ber. 13, 20 (1880) that on treatment with molten alkali, 2-aminobenzothiazoles are irreversibly split into o-aminothiophenolates and ammonia and alkali metal carbonates, the heterocycle being destroyed in this reaction. In contrast thereto, a gentle ring opening is ensured in accordance with the present invention, in which process practically no ammonia escapes, and the alkali metal salts or alkaline earth metal salts of the corresponding o-mercaptophenylureas (see formula (2) above) are obtained as intermediates with high, often nearly quantitative, yields. These stable mercaptides of the formula (2) can subsequently be converted, either directly of after intermediate isolation, to the 2-hydroxybenzothiazoles by treatment with acid.

This acid-catalytic cyclization of the compounds of the formulae (2) and (3), respectively, to form the 2-hydroxybenzothiazoles of the formula (4), although known from J. Chem. Soc. 1962,230, has not been realized hitherto on an industrial scale, because preparation of the starting compounds of the formula (3) was possible only by reaction of ortho-aminothiophenols with excess sodium cyanate, in which reaction the cited ecological and synthesis problems were involved.

By finding the new process for the preparation of the key compounds of the formulae (2) and (3), respectively, 2-hydroxybenzothiazole compounds can be manufactured now in a simple and technically advantageous manner from easily obtainable precursors.

Suitable 2-aminobenzothiazole compounds serving as starting material are preferably those which are described in German Offenlegungsschrift No. 2,801,991. Especially preferred according to the process of the invention is the manufacture of 2-hydroxybenzothiazoles of the formula (4a)

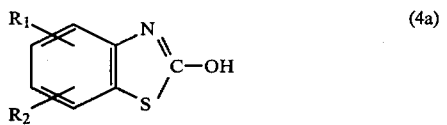

(4a)

in which $R_1$ and $R_2$ are identical or different and represent each a hydrogen atom, an alkyl group, preferably a lower alkyl group, an alkoxy group, preferably a lower alkoxy group, a halogen atom, preferably fluorine or chlorine, a hydroxy or sulfo group, while starting according to the invention from 2-aminobenzothiazoles of the formula (1a)

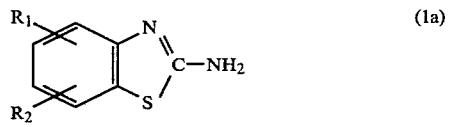

(1a)

in which $R_1$ and $R_2$ are as defined above.

The process according to the invention of ring cleavage of the 2-aminobenzothiazoles to yield the o-mercaptophenylureas must be carried out in an anhydrous or practically anhydrous medium in order to ensure high yields. Although small amounts of water contained in the solvents or diluents may be present, the yield and possibly the purity of the products, however, is decreased in this case. It is therefore recommended in accordance with the invention to carry out the ring cleavage of the 2-aminobenzothiazoles with substantial exclusion of water.

The reaction temperature of the process step according to the invention for obtaining the compounds of the formula (2) is in a range of from 80° to 200° C.; preferably from 120° to 160° C. When low-boiling solvents or diluents are used, such as alkanols having 1 to 3 carbon atoms, or lower glycolmonoalkyl ethers, the reaction should be carried out in a closed system and under pressure.

The alkali metal or alkaline earth metal hydroxide is used for the ring cleavage reaction in an at least stoichiometric amount. In order to prevent side reactions, an excess of an 1- to 4-fold, preferably 2- or 3-fold, molar amount of alkali metal or alkaline earth metal hydroxide has proved to be favorable.

The alkali metal or alkaline earth metal salts of ortho-mercaptophenylureas prepared according to the invention are subsequently converted with acid to the ortho-thiophenylurea compounds, optionally after separation from the reaction medium by removal of the solvent or diluent. Equivalent amounts of acid are required for this step. The subsequent cyclization of these thiophenylureas to yield the 2-hydroxybenzothiazoles can be carried out with catalytic or excess amounts of acid, in a solvent or diluent, preferably, however, in the aqueous medium of the acid applied. The temperature of this cyclization reaction is in a range of from 40° to 100° C., preferably 60° to 90° C. The reaction is complete within a short period of time.

The process of the invention may be carried out as follows: A 2-aminobenzothiazole compound, for example of the formula (1) or (1a), is heated, while stirring, in an anhydrous or practically anhydrous solvent, for example ethanol, isobutanol, 1,2-dihydroxypropane or 1,3-dihydroxypropane, preferably ethyleneglycol, glycerol, ethyleneglycol-monomethyl ether or ethyleneglycol-monoethyl ether, together with the solid alkali metal or alkaline earth metal hydroxide, preferably sodium hydroxide, to a temperature of from 120° to 160° C., and the reaction is allowed to proceed for several hours within this temperature range. The complete conversion can be stated by chromatographic analysis for starting material. Practically no ammonia escapes in this ring opening reaction. The alkali metal or alkaline earth metal salt of the o-mercaptophenylurea compound formed precipitates in crystallized form from the reaction mixture; it can be separated by filtration from the optionally recyclizable mother liquor and subjected to the cyclization reaction. On the other hand, the salt of o-mercaptophenylurea compound formed can be left in the reaction medium and directly converted to the free o-mercaptophenylurea compound by adding an at least stoichiometric amount of mineral acid, relative to alkali metal or alkaline earth metal hydroxide used, which free compound can be isolated by filtration, for example after addition of water. However, due to the instability of these free o-mercaptophenylurea compounds, it is recommended to cyclize them or their salts directly in the acidic medium by a short-time heating in order to form the intended 2-hydroxybenzothiazole compound. In this latter case, the final product is isolated either by filtration from the solvent used, optionally after further dilution with water, or by blowing off the solvent and subsequently mechanically separating the suspension obtained, for example by means of filter press, separator or centrifuge. When starting from the isolated salt of o-mercaptophenylurea compound or the isolated free mercapto compound for the cyclization, these compounds are dissolved or suspended in water which may contain a further solvent or diluent; after addition of acid until an acidic pH has adjusted, this mixture is heated to 40°–100° C., preferably 60° to 90° C.

In some cases, the operations may alternatively be as follows: after the ring cleavage, the solvent or diluent is distilled off from the alkaline reaction mixture or blown off by means of steam, and acid, preferably aqueous acid, is added to the salt of o-mercaptophenylurea compound or the aqueous solution thereof until the pH has adjusted in the acidic range, and the batch is then heated in the above temperature range.

The process of the invention starts from compounds easily obtainable on an industrial scale, and furnishes the corresponding 2-hydroxybenzothiazole compounds with high yield and quality, in technologically simple operation steps and in an ecologically favorable manner.

The following examples illustrate the invention; parts and percentages being by weight unless otherwise stated. The relation of parts by weight to parts by volume is that of kilogram to liter.

EXAMPLE 1

A mixture of 150 parts of 2-hydroxybenzothiazole, 150 parts of solid sodium hydroxide and 300 parts of ethyleneglycol is stirred for 6 hours at 130°–140° C., subsequently cooled to 80° C., and introduced with agitation into 3000 parts of icewater. After 30 minutes, 5 parts of active charcoal are added for clarification, the solution is stirred for a further 15 minutes and then filtered. The pH of the filtrate is adjusted to 5–6 by means of 10% aqueous hydrochloric acid, and the precipitated 2-mercaptophenylurea is isolated by filtration (The dried product is obtained with a yield of 92% of theory and has a melting point of 151°–153° C.). The isolated moist product is immediately introduced into 700 parts of a 10% aqueous hydrochloric acid and heated for 15 minutes with agitation at 90° C. The thus precipitating 2-hydroxybenzothiazole is isolated by filtration after having cooled the acidic batch, washed with water and dried. 135 Parts of an analytically pure product having a melting point of 137°–139° C. are obtained; this corresponds to a yield of 90% of theory, relative to 2-aminobenzothiazole.

EXAMPLE 2

Operations are as in Example 1, but instead of the 150 parts of sodium hydroxide, equivalent parts of solid potassium hydroxide or barium hydroxide are used in the reaction. The 2-hydroxybenzothiazole is obtained with an about similar yield and quality.

EXAMPLE 3

A mixture of 82 parts of 4-methyl-2-aminobenzothiazole, 50 parts of solid sodium hydroxide and 75 parts of glycerol is stirred for 12 hours at 130° C., and subsequently slowly introduced into 1000 parts of icewater. The solution of sodium salt of 6-methyl-2-mercaptophenylurea so obtained is clarified after addition of 2.5 parts of active charcoal. 250 Parts of a 30% aqueous hydrochloric acid are added to the filtrate, and the batch is heated for 15 minutes with agitation at 85°–90° C., and then cooled to 20° C. The precipitated 4-methyl-2-hydroxy-benzothiazole is isolated by filtration, washed with water and dried. 78.8 Parts of an analytically pure product having a melting point of 213°–214° C. are obtained, which corresponds to a yield of 95.5% of theory.

EXAMPLE 4

Operations are as described in Example 3; however, the hydrochloric acid used there for the cyclization reaction is replaced by an equivalent amount of sulfuric or phosphoric acid. A product of identical purity and yield is obtained.

EXAMPLE 5

Operations are as in Example 3; however, instead of glycerol as solvent there is used an identical amount of 1,2-dihydroxypropane or 1,3-hydroxypropane. After hydrolysis, the 4-methyl-2-hydroxybenzothiazole is obtained with similar yield and quality.

EXAMPLE 6

A mixture of 92.25 parts of 6-chloro-2-aminobenzothiazole, 60 parts of solid sodium hydroxide and 150 parts of isobutanol is stirred for 9 hours at 140° C. in a stainless steel autoclave. After cooling, the suspension of sodium salt of 4-chloro-2-mercapto-phenylurea obtained is filtered off, the filter residue is washed with isobutanol and dried. The salt, obtained with a yield of 93.2% of theory, is introduced into 400 parts of a 10% aqueous hydrochloric acid. The suspension is heated for 30 minutes at 80° C., thus causing first solution of the salt and subsequently precipitation of the colorless 6-chloro-2-hydroxybenzothiazole which is filtered after cooling of the acid batch, washed with water and dried. 81.8 Parts, corresponding to a yield of 88.2% of th., of a practically analytically pure product having a melting point of 203°–204° C. are obtained.

When this operation mode is varied in that the isolated sodium salt of 4-chloro-2-mercaptophenylurea is left in moist state containing the isobutanol, and is introduced, without being dried, into the cited amount of hydrochloric acid, and this suspension is heated for 30 minutes at 80° C., and the work-up is performed analogously, optionally with blowing-off of the isobutanol entrained with the mercapto compound, 83 parts of 6-chloro-2-hydroxybenzothiazole (corresponding to a yield of 89.5% of th.) having a melting point of 202°–203° C., are obtained.

EXAMPLE 7

Operations are as indicated in the first paragraph of Example 6; however, the solvent isobutanol is replaced by an identical amount of n-butanol or ethanol or glycol-monomethyl ether. These process variants give 6-chloro-2-hydroxybenzothiazole with an about identical purity and yield.

EXAMPLE 8

A mixture of 99.25 parts of 4-methyl-7-chloro-2-aminobenzothiazole, 100 parts of ethyleneglycol and 60 parts of solid sodium hydroxide is heated for 4 hours with agitation at 160° to 165° C. Subsequently, the batch is cooled with agitation to a temperature of 20°–30° C., and the precipitated sodium salt of 6-methyl-3-chloro-2-mercaptophenylurea is isolated by suction-filtration. The glycolic filtrate can be reused for the next reaction batch.

The filter residue is washed with 20 parts of glycol and then introduced in 300 parts of a 10% aqueous hydrochloric acid. This mixture is then heated for 60 minutes with agitation at 80°–85° C. After cooling, the precipitated 7-chloro-4-methyl-2-hydroxybenzothiazole is isolated by filtration, washed with water to neutral and dried. 62.4 Parts (corresponding to a yield of 62.5% of th.) of an analytically pure product having a melting point of 265.5°–266° C. are obtained.

When the glycolic reaction mixture is worked up according to Example 1, the 7-chloro-4-methyl-2-hydroxybenzothiazole is obtained in practically identical purity with a yield of 85.6% of th.

EXAMPLE 9

A mixture of 99.25 parts of 4-methyl-7-chloro-2-aminobenzothiazole, 20 parts of solid sodium hydroxide and the glycolic mother liquor mentioned in Example 8 is heated for 4 hours with agitation at 160°–165° C. The batch is then cooled with agitation to a temperature of 20°–30° C., and operations for cyclization of the precipitated sodium salt of 6-methyl-3-chloro-2-mercaptophenylurea are as indicated in Example 8. 85 Parts of 7-chloro-4-methyl-2-hydroxybenzothiazole having a melting point of 265.5°–266° C. are obtained, which corresponds to a yield of 85.2% of th.

EXAMPLE 10

Operations are as indicated in Example 8 and subsequently as in Example 9; however, the starting compound 4-methyl-7-chloro-2-aminobenzothiazole is replaced by the equivalent amount of 4-chloro-2-aminobenzothiazole. Via the intermediate stage of sodium salt of 6-chloro-2-mercaptophenylurea the 4-chloro-2-hydroxybenzothiazole is obtained as final product with a yield of 59.3% of theory according to the operation mode of Example 8 and of 84.0% of theory according to the operation mode of Example 9; the melting point being 204.5° to 205° C. in each case.

EXAMPLES 11 TO 19

When preparing a 2-hydroxybenzothiazole compound according to the invention, for example as described in the above Examples, while using as starting compound a 2-aminobenzothiazole compound according to formula (1a) the radicals $R_1$ and $R_2$ of which are indicated in the following Table, the corresponding 2-hydroxybenzothiazole compound of formula (4a) having the corresponding substituents $R_1$ and $R_2$ also indicated in the Table is obtained with the yield and melting point as further indicated in the Table.

| Ex. | Compound (1a) $R_1$ | $R_2$ | Compound (4a) $R_1$ | $R_2$ | Yield (% of th.) | m.p. °C. |
|---|---|---|---|---|---|---|
| 11 | 6-methyl | H | 6-methyl | H | 89.1 | 168.5–170 |
| 12 | 6-bromo | H | 6-bromo | H | 79.4 | 222–223 |
| 13 | 4-methyl | 6-chloro | 4-methyl | 6-chloro | 85.7 | 243.5–224 |
| 14 | 6-hydroxy | H | 6-hydroxy | H | 79.2 | 240–242 |
| 15 | 6-methoxy | H | 6-methoxy | H | 84.3 | 162.5–164 |
| 16 | 4-methoxy | H | 4-methoxy | H | 78.7 | 170–171.5 |
| 17 | 6-ethoxy | H | 6-ethoxy | H | 86.9 | 145.5–146.5 |
| 18 | 4-methyl | 6-methyl | 4-methyl | 6-methyl | 88.4 | 216–217 |
| 19 | 6-sulfo | H | 6-sulfo | H | 77.4 | >300 |

What is claimed is:

1. A process for the manufacture of a 2-hydroxybenzothiazole compound which comprises reacting at a temperature within the range of 80°–200° C. a 2-aminobenzothiazole compound with an alkali metal hydroxide or alkaline earth metal hydroxide in a substantially anhydrous solvent or diluent medium stable to alkalis, said medium containing less than about 2.5 weight % of water, relative to the reaction mixture, and cyclizing the alkali metal or alkaline earth metal salt of the ortho-mercapto-N-phenylurea compound so obtained, by heating the ortho-mercapto-N-phenylurea compound with an acid to a temperature in the range from 40° to 100° C.

2. A process according to claim 1 wherein the temperature within the range of 80°–200° C. is 120°–160° C.

3. A process according to claim 1 or 2 which is carried out in the absence of water.

4. A process according to claim 1 or 2 wherein the cyclization step is carried out without isolation of the ortho-mercapto-N-phenylurea compound.

5. A process according to claim 1 or 2 wherein said 2-aminobenzothiazole compound has the formula:

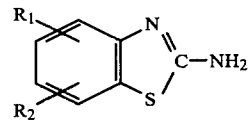

wherein $R_1$ and $R_2$ are identical or different and each represent a hydrogen atom, an alkyl group, or alkoxy group, a halogen atom, a hydroxy group, or a sulfo group, and the 2-hydroxybenzothiazole obtained therefrom has the formula:

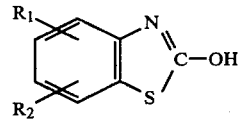

wherein $R_1$ and $R_2$ are as defined previously.

* * * * *